(12) United States Patent
Nettekoven et al.

(10) Patent No.: US 6,514,989 B1
(45) Date of Patent: Feb. 4, 2003

(54) AROMATIC AND HETEROAROMATIC SUBSTITUTED 1,2,4-TRIAZOLO PYRIDINE DERIVATIVES

(75) Inventors: Matthias Heinrich Nettekoven, Grenzach-Wyhlen (DE); Bernd Puellmann, Aesch (CH)

(73) Assignee: Hoffmann-La Roche Inc., Nutley, NJ (US)

( * ) Notice: Subject to any disclaimer, the term of this patent is extended or adjusted under 35 U.S.C. 154(b) by 0 days.

(21) Appl. No.: 10/157,346

(22) Filed: May 29, 2002

(30) Foreign Application Priority Data

Jul. 20, 2001 (EP) .............................. 01117539

(51) Int. Cl.[7] ...................... A61K 31/435; C07D 47/04
(52) U.S. Cl. ........................ 514/303; 546/119
(58) Field of Search ........................... 546/119; 514/302

(56) References Cited

FOREIGN PATENT DOCUMENTS

| EP | 972 774 | 1/2000 |
|---|---|---|
| WO | WO 94/14812 | 7/1994 |
| WO | WO 01/17999 | 3/2001 |

OTHER PUBLICATIONS

Poulsen et al., *Bioorganic & Med. Chemistry*, vol. 6, pp. 619–641 (1998).
Mueller et al., *Bioorganic & Med.Chemistry*, vol. 6, pp. 707–719 (1998).
Kim et al., *J. Med. Chem.*, vol. 41, pp. 2835–2845 (1998).
Li et al., *J. Med. Chem.*, vol. 41, pp. 3186–3201 (1998).
Baraldi et al., *J. Med. Chem.*, vol. 41, pp. 2126–2133 (1998).
Li et al., J. Med. Chem., vol. 42, pp. 706–721 (1999).
Baraldi et al., J. Med. Chem., vol. 39, pp. 1164–1171 (1996).
Collotta et al., Arch. Pharm. Med. Chem., vol. 332, pp. 39–41 (1999).

*Primary Examiner*—Bernard Dentz
(74) *Attorney, Agent, or Firm*—George W. Johnston; Patricia S. Rocha-Tramaloni; Arthur D. Dawson

(57) ABSTRACT

The invention is a compound of formula

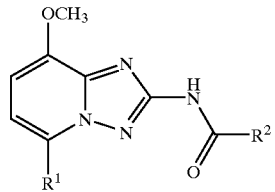

I or a pharmaceutically acceptable salt thereof, wherein $R^1$ and $R^2$ are as defined in the specification. A compound of formula I has a good affinity to the adenosine receptor and can therefore be used for the treatment or protection of diseases mediated by this receptor.

14 Claims, No Drawings

AROMATIC AND HETEROAROMATIC SUBSTITUTED 1,2,4-TRIAZOLO PYRIDINE DERIVATIVES

FIELD OF THE INVENTION

The present invention relates to compounds of formula

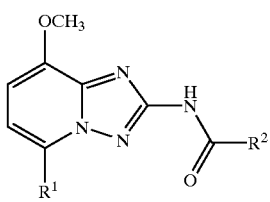

I wherein $R^1$ and $R^2$ are each selected from the group consisting of unsubstituted thiophenyl, unsubstituted phenyl, substituted thiophenyl and substituted phenyl. The compounds of formula I are adenosine receptor ligands useful in the treatment of diseases such as, e.g., Alzheimer's, Parkinson's and schizophrenia.

BACKGROUND

Adenosine modulates a wide range of physiological functions by interacting with specific cell surface receptors. The potential of adenosine receptors as drug targets was first reviewed in 1982. Adenosine is related both structurally and metabolically to several bioactive nucleotides. These bioactive nucleotides include adenosine triphosphate (ATP); adenosine diphosphate (ADP); adenosine monophosphate (AMP) and cyclic adenosine monophosphate (cAMP); the biochemical methylating agent S-adenosyl-L-methione (SAM); structurally to the coenzymes NAD, FAD and coenzyme A; and to RNA. Together adenosine and these related compounds are important in the regulation of many aspects of cellular metabolism and in the modulation of different central nervous system activities.

The receptors for adenosine have been classified as $A_1$, $A_{2A}$, $A_{2B}$ and $A_3$ receptors, belonging to the family of G protein-coupled receptors. Activation of adenosine receptors by adenosine initiates signal transduction mechanism. These mechanisms are dependent on the receptor associated G protein. Each of the adenosine receptor subtypes has been classically characterized by the adenylate cyclase effector system, which utilizes cAMP as a second messenger. The $A_1$ and $A_3$ receptors, coupled with $G_i$ proteins inhibit adenylate cyclase, leading to a decrease in cellular cAMP levels, while $A_{2A}$ and $A_{2B}$ receptors couple to $G_S$ proteins and activate adenylate cyclase, leading to an increase in cellular cAMP levels. It is known that the $A_1$ receptor system include the activation of phospholipase C and modulation of both potassium and calcium ion channels. The $A_3$ subtype, in addition to its association with adenylate cyclase, also stimulates phospholipase C and so activates calcium ion channels.

The $A_1$ receptor (326–328 amino acids) was cloned from various species (canine, human, rat, dog, chick, bovine, guinea-pig) with 90–95% sequence identify among the mammalian species. The $A_{2A}$ receptor (409–412 amino acids) was cloned from canine, rat, human, guinea pig and mouse. The $A_{2B}$ receptor (332 amino acids) was cloned from human and mouse with 45% homology of human $A_{2B}$ with human $A_1$ and $A_{2A}$ receptors. The $A_3$ receptor (317–320 amino acids) was cloned from human, rat, dog, rabbit and sheep.

The $A_1$ and $A_{2A}$ receptor subtypes are proposed to play complementary roles in adenosine's regulation of the energy supply. Adenosine, which is a metabolic product of ATP, diffuses from the cell and acts locally to activate adenosine receptors to decrease the oxygen demand ($A_1$) or increase the oxygen supply ($A_{2A}$) and so reinstate the balance of energy supply versus demand within the tissue. The actions of both subtypes is to increase the amount of available oxygen to tissue and to protect cells against damage caused by a short-term imbalance of oxygen. One of the important functions of endogenous adenosine is preventing damage during traumas such as hypoxia, ischaemia, hypotension and seizure activity.

Furthermore, it is known that the binding of the adenosine receptor agonist to mast cells expressing the rat $A_3$ receptor resulted in increased inositol triphosphate and intracellular calcium concentrations, which potentiated antigen induced secretion of inflammatory mediators. Therefore, the $A_3$ receptor plays a role in mediating asthmatic attacks and other allergic responses.

Adenosine is also a neuromodulator, possessing global importance in the modulation of molecular mechanisms underlying many aspects of physiological brain function by mediating central inhibitory effects. An increase in neurotransmitter release follows traumas such as hypoxia, ischaemia and seizures. These neurotransmitters are ultimately responsible for neural degeneration and neural death, which causes brain damage or death of the individual. The adenosine $A_1$ agonists which mimic the central inhibitory effects of adenosine may therefore be useful as neuroprotective agents. Adenosine has been proposed as an endogenous anticonvulsant agent, inhibiting glutamate release from excitatory neurons and inhibiting neuronal firing. Adenosine agonists therefore may be used as antiepileptic agents. Adenosine antagonists stimulate the activity of the CNS and have proven to be effective as cognition enhancers. Selective $A_{2a}$-antagonists have therapeutic potential in the treatment of various forms of dementia, for example in Alzheimer's disease and are useful as neuroprotective agents. Adenosine $A_2$-receptor antagonists inhibit the release of dopamine from central synaptic terminals and reduce locomotor activity and consequently improve Parkinsonian symptoms. The central activities of adenosine are also implicated in the molecular mechanism underlying sedation, hypnosis, schizophrenia, anxiety, pain, respiration, depression and substance abuse. Drugs acting at adenosine receptors therefore have also therapeutic potential as sedatives, muscle relaxants, antipsychotics, anxiolytics, analgesics, respiratory stimulants and antidepressants.

An important role for adenosine in the cardiovascular system is as a cardioprotective agent. Levels of endogenous adenosine increase in response to ischaemia and hypoxia, and protect cardiac tissue during and after trauma (preconditioning). Adenosine agonists thus have potential as cardioprotective agents.

Adenosine modulates many aspects of renal function, including renin release, glomerular filtration rate and renal blood flow. Compounds, which antagonize the renal affects of adenosine, have potential as renal protective agents. Furthermore, adenosine $A_3$ and/or $A_{2B}$ antagonists may be useful in the treatment of asthma and other allergic responses.

Numerous documents describe the current knowledge on adenosine receptors, for example the following publications:
Bioorganic & Medicinal Chemistry, 6, (1998), 619–641,
Bioorganic & Medicinal Chemistry, 6, (1998), 707–719,
J. Med. Chem., (1998), 41, 2835–2845,
J. Med. Chem., (1998), 41, 3186–3201,
J. Med. Chem., (1998), 41, 2126–2133,
J. Med. Chem., (1999), 42, 706–721,
J. Med. Chem., (1996), 39, 1164–1171,
Arch. Pharm. Med. Chem., (1999), 332, 39–41.

SUMMARY

The present invention is a compound of formula

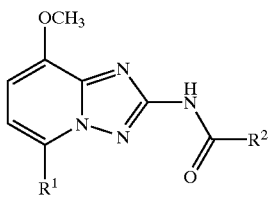

I or a pharmaceutically acceptable salt thereof, wherein
$R^1$ is selected from the group consisting of unsubstituted phenyl, unsubstituted thiophenyl and phenyl or thiophenyl substituted by one or two substituents selected from the group consisting of
halogen, trifluoromethyl, lower alkyl, lower alkoxy, acetlylamino, acetyl, lower alkenyl, —C(O)O-lower alkyl, and thio-lower alkyl; and
$R^2$ is selected from the group consisting of unsubstituted phenyl, unsubstituted thiophenyl and phenyl or thiophenyl substituted by one or two substitutents selected from the group consisting of
halogen , lower alkyl, halogen-lower alkyl and lower alkoxy.

It has surprisingly been found that the compounds of formula I are adenosine receptor ligands.

A compound of formula I, or a pharmaceutically acceptable salt thereof, is an object of the present invention. Another object of the invention is a pharmaceutical composition containing a therapeutically effective amount of a compound of formula I or a pharmaceutically acceptable salt thereof. The manufacture of a compound of formula I and a pharmaceutical composition containing a compound of formula I is an object of the invention. Yet another object of the invention is a method of treatment for the control or prevention of illnesses based on the modulation of the adenosine system, such as Alzheimer's disease, Parkinson's disease, neuroprotection, schizophrenia, anxiety, pain, respiration deficits, depression, asthma, allergic responses, hypoxia, ischaemia, seizure and substance abuse comprising administering an effective amount of a compound of formula I, or a pharmaceutically acceptable salt thereof, to a patient in need of such treatment. The method of treatment of the invention includes a administering a therapeutically effective amount of a compound of the present invention as a sedative, muscle relaxant, antipsychotic, antiepileptic, anticonvulsant and cardioprotective agent. The most preferred indications in accordance with the method of treatment of the invention are those, which are based on the $A_{2A}$ receptor antagonistic activity of a compound of formula I that include disorders of the central nervous system, for example the treatment or prevention of certain depressive disorders, neuroprotection and Parkinson's disease.

DETAILED DESCRIPTION

As used herein, the term "lower alkyl" denotes a saturated straight- or branched-chain alkyl group containing from 1 to 6 carbon atoms, for example, methyl, ethyl, propyl, isopropyl, n-butyl, i-butyl, 2-butyl, t-butyl and the like. Preferred lower alkyl groups are groups with 1–4 carbon atoms.

As used herein, the term "lower alkenyl" denotes an unsaturated straight- or branched-chain, containing 2 to 6 carbon atoms and at least one double bond, for example, ethylen, propylen, isopropylen, n-butylen, i-butylen, 2-butylen, t-butylen and the like. Preferred lower alkenyl groups are groups with 2–4 carbon atoms.

The term "halogen" denotes chlorine, iodine, fluorine and bromine.

The term "lower alkoxy" denotes a group wherein the alkyl residues is as defined above, and which is attached via an oxygen atom.

"Acetylamino" means the group —NHC(O)CH$_3$ and "acetyl" is —C(O)CH$_3$. The term "pharmaceutically acceptable acid addition salts" embraces salts with pharmaceutically acceptable inorganic and organic acids, such as hydrochloric acid, nitric acid, sulfuric acid, phosphoric acid, citric acid, formic acid, fumaric acid, maleic acid, acetic acid, succinic acid, tartaric acid, methane-sulfonic acid, p-toluenesulfonic acid and the like.

A preferred compound of formula I of the present invention is, wherein $R^1$ is unsubstituted thiophenyl; and $R^2$ is selected from the group consisting of unsubstituted phenyl, and phenyl substituted by halogen or lower alkyl. An exemplary preferred compound is selected from the group consisting of 4-bromo-N-(8-methoxy-5-thiophen-2-yl-[1,2,4]triazolo[1,5-a ]pyridin-2-yl)-benzamide, N-(8-methoxy-5-thiophen-2-yl-[1,2,4]triazolol[1,5-a]pyridin-2-yl)-benzamide, 3-chloro-N-(8-methoxy-5-thiophen-2-yl-[1,2,4]triazolo[1,5-a]pyridin-2-yl)-benzamide, 4-chloro-N-(8-methoxy-5-thiophen-2-yl-[1,2,4]triazolo[1,5-a]pyridin-2-yl)-benzamide and 4-ethyl-N-(8-methoxy-5-thiophen-2-yl-[1,2,4]triazolo[1,5-a]pyridin-2-yl)-benzamide.

Further preferred is a compound, wherein $R^1$ is selected from the group consisting of unsubstituted phenyl and phenyl substituted by lower alkoxy; and wherein $R^2$ is selected from the group consisting of unsubstituted phenyl and phenyl substituted by halogen. An exemplary further preferred compound is selected from the group consisting of 4-fluoro-N-(8-methoxy-5-phenyl-[1,2,4]triazolo[1,5-a] pyridin-2-yl)-benzamide, 3-bromo-N-(8-methoxy-5-phenyl-[1,2,4]triazolo[1,5-a]pyridin-2-yl)-benzamide, 4-bromo-N-(8-methoxy-5-phenyl-[1,2,4]triazolo[1,5-a]pyridin-2-yl)-benzamide and N-[5-(3-ethoxy-phenyl)-8-methoxy-[1,2,4]triazolo[1,5-a]pyridin-2-yl]-4-fluoro-benzamide.

An additional preferred compound of formula I of the present invention is wherein $R^1$ is selected from the group consisting of unsubstituted phenyl and phenyl substituted by halogen or lower alkoxy; and $R^2$ is thiophenyl, unsubstituted or substituted by lower alkyl. An exemplary additional preferred compound is selected from the group consisting of 5-methyl-thiophene-2-carboxylic acid (8-methoxy-5-phenyl-[1,2,4]triazolo[1,5-a]pyridin-2-yl)-amide,
   5-methyl-thiophene-2-carboxylic acid [5-(2-fluoro-phenyl)-8-methoxy-[1,2,4]triazolo[1,5-a]pyridin-2-yl]-amide,
   5-methyl-thiophene-2-carboxylic acid [8-methoxy-5-(3-methoxy-phenyl)-[1,2,4]triazolo[1,5-a]pyridin-2-yl]-amide,
   5-methyl-thiophene-2-carboxylic acid [8-methoxy-5-(4-methoxy-phenyl)-[1,2,4]triazolo[1,5-a]pyridin-2-yl]-amide,
   5-methyl-thiophene-2-carboxylic acid [5-(3-ethoxy-phenyl)-8-methoxy-[1,2,4]triazolo[1,5-a]pyridin-2-yl]-amide and
   5-methyl-thiophene-2-carboxylic acid [5-(3-fluoro-phenyl)-8-methoxy-[1,2,4]triazolo[1,5-a]pyridin-2-yl]-amide.

further preferred compound is, wherein $R^1$ is selected from the group consisting of unsubstituted thiophenyl and thiophenyl substituted by halogen; and wherein $R^2$ is selected from the group consisting of unsubstituted thiophenyl, and thiophenyl substituted by lower alkyl. An exemplary further preferred compound is selected from the group consisting of 5-methyl-thiophene-2-carboxylic acid (8-methoxy-5-thiophen-3-yl-[1,2,4]triazolo[1,5-a]pyridin-2-yl)-amide and 5-methyl-thiophene-2-carboxylic acid [5-(5-chloro-thiophen-2-yl)-8-methoxy-[1,2,4]triazolo[1,5-a] pyridin-2-yl]-amide.

The present compounds of formula I and their pharmaceutically acceptable salts can be prepared by methods known in the art, for example, by processes described below, which process comprises reacting a compound of formula

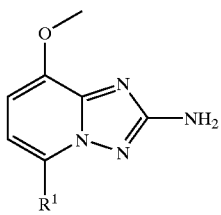

II with a compound of formula $R^2COCl$

III forming a compound of formula

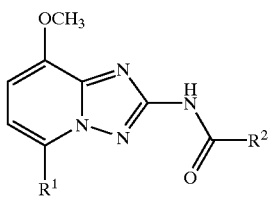

I wherein $R^1$ and $R^2$ are defined above. or reacting a compound of formula

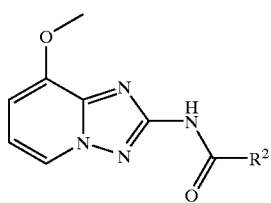

IV with $KIO_3$ forming a compound of formula

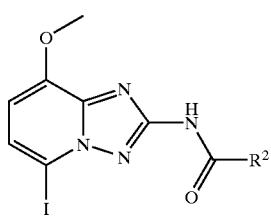

V and then with a compound of formula

  VIa

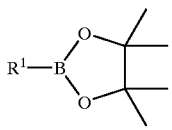  VIb forming a compound of formula

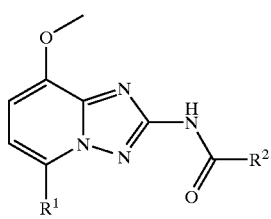

I wherein $R^1$ and $R^2$ are as defined above. or modifying one or more substituents $R^1$ or $R^2$ within the definitions given above, and if desired, converting the compounds obtained into pharmaceutically acceptable acid addition salts.

In Examples 1–51 and in the following scheme 1 the preparation of compounds of formula I is described in more detail.

The following abbreviations have been used:

DMSO dimethyl sulfoxide

DMF N,N-dimethylformamide

DMAP 4-dimethylaminopyridine

DCM 4-(dicyanomethylene)-2-methyl-6-(4-dimethylaminostyryl)-4H-pyran

THF tetrahydrofuran

Scheme 1
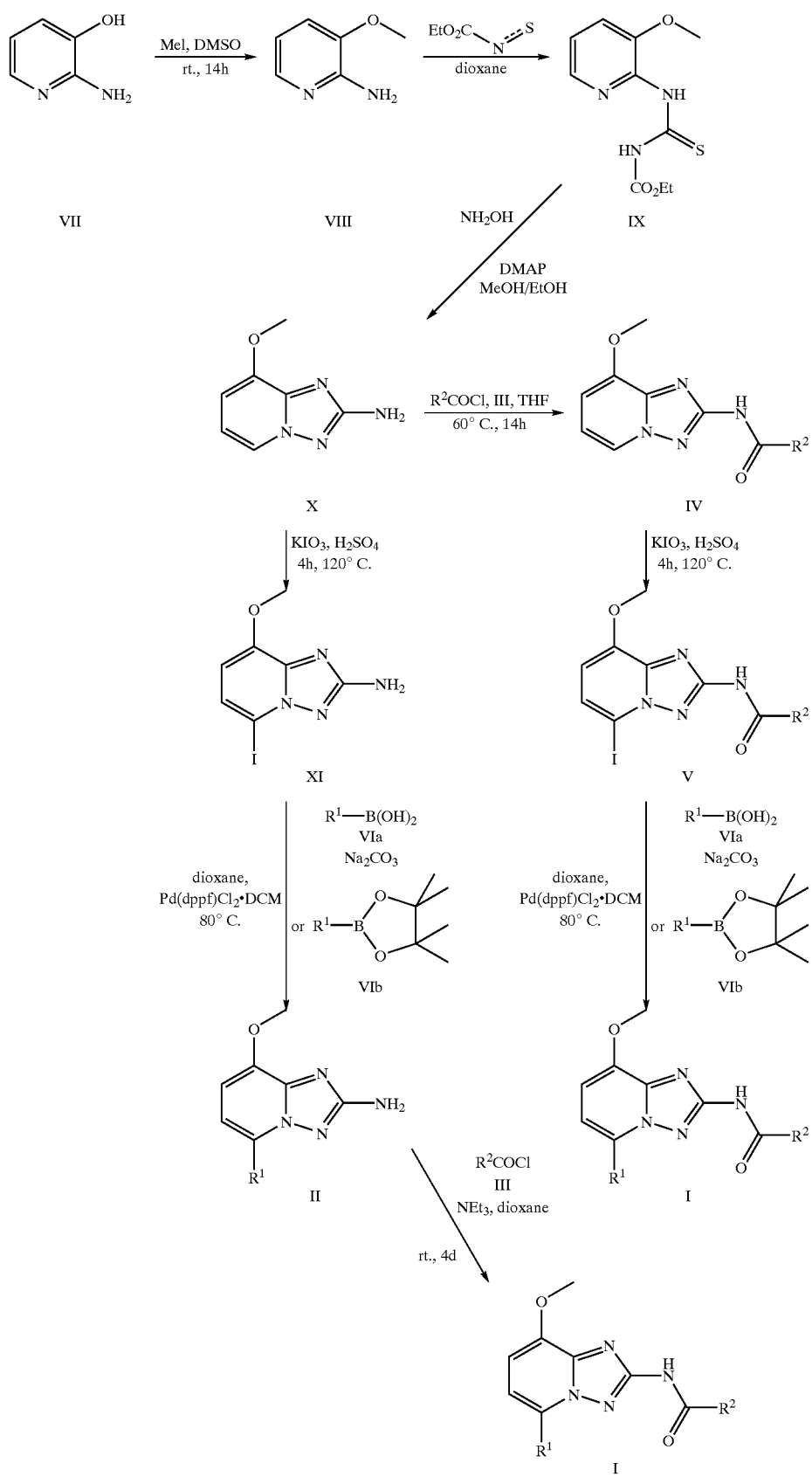

wherein $R^1$ and $R^2$ are defined above.

Scheme 1 describes the process for preparation of 8-methoxy-[1,2,4]triazolo [1,5-a]pyridine derivatives, starting from the compound of formula VII (commercially available). To a suspension of KOH and DMSO is added 2-amino-3-hydroxypyridine (VII) and the solution is stirred. Then methyl iodide is added to give a compound of formula VIII. A mixture of compound VIII and ethoxycarbonyl isothiocyanate in dioxane is stirred at room temperature to give a compound of formula IX. Then to a solution of hydroxylamine hydrochloride and N-ethyldiisopropylamine in a mixture of methanol/ethanol is added N-(3-methoxy-2-pyridinyl)-N'-carboethoxy-thiourea to give the compound of formula X. This compound (8-methoxy-[1,2,4]triazolo[1,5-a]pyridin-2-yl-amide) is then solved in a compound of formula $R^2COCl$ (III), to obtain a compound of formula IV. A compound of formula III may be: benzoyl chloride, 4-F-benzoyl chloride, cyclohexane chlorocarbonyl and the like.

Furthermore, a compound of formula X may be solved in sulfuric acid and then heated to about 100° C. and $KIO_3$ is added in portions over a period of 1 h. Then the iodide atom from the obtained compound of formula X is replaced by the substituent $R^1$, starting from 8-methoxy-5-iodo-[1,2,4]triazolo[1,5-a]pyridin-2-yl-amine and a respective boronic acid or ester, for example as indicated in the following list

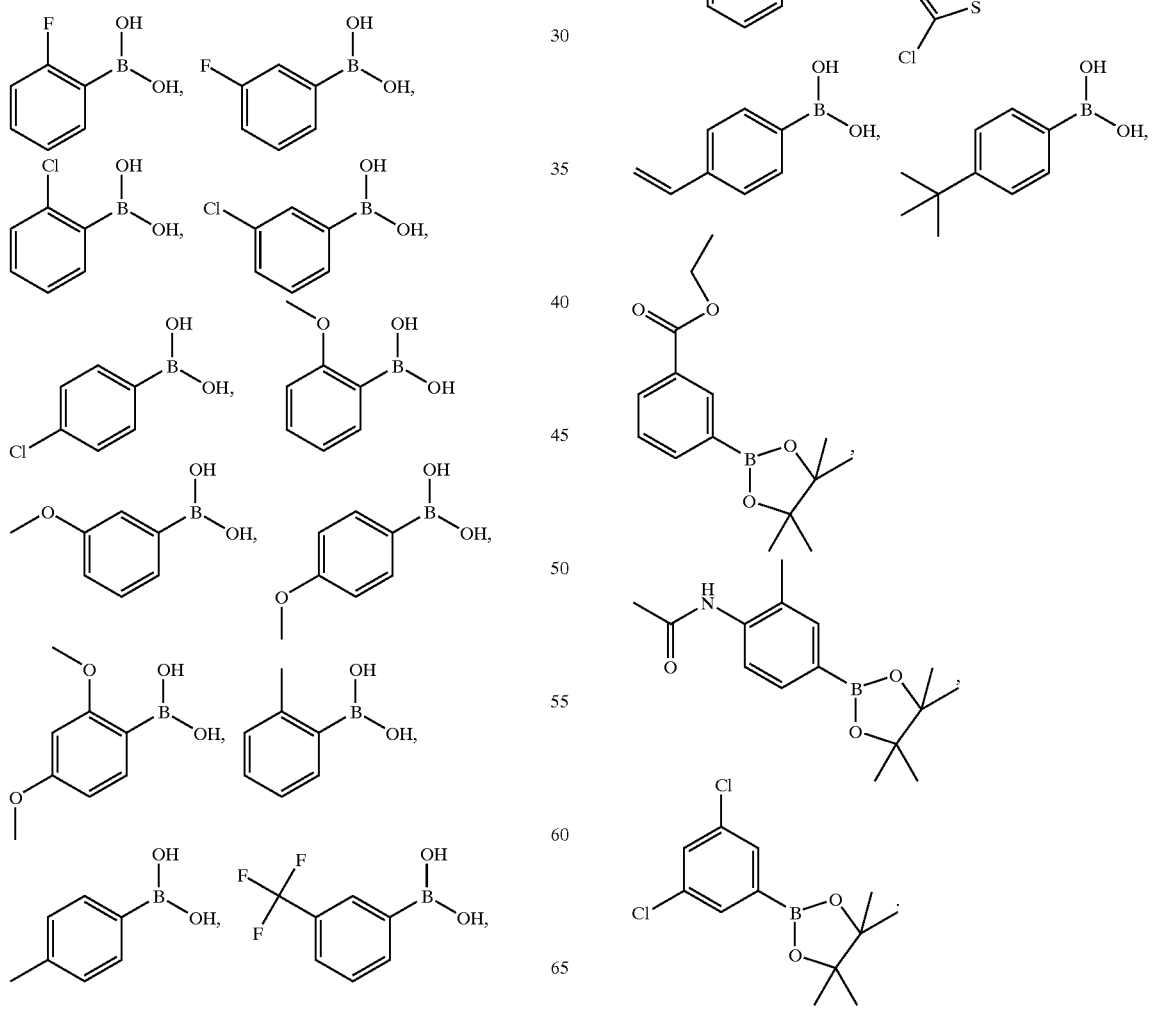

A compound of formula I is obtained.

The salt formation is effected at room temperatures in accordance with methods which are known and familiar to any person skilled in the art. Not only salts with inorganic acids, but also salts with organic acids came into consideration. Hydrochlorides, hydrobromides, sulfates, nitrates, citrate, acetates, maleates, succinates, methansulfonates, p-toluenesulfonates and the like are examples of such salts.

The compounds of formula I and their pharmaceutically usable addition salts possess valuable pharmacological properties. Specifically, it has been found that the compounds of the present invention are adenosine receptor ligands.

The compounds were investigated in accordance with the tests given hereinafter.

Human Adenosine $A^1$ Receptor

The gene encoding human adenosinie $A_1$ receptor was recombinantly introduced and expressed in chinese hamster ovary (CHO) cells using the semliki forest virus expression system. Cells were harvested, washed twice by centrifugation, homogenized and again washed by centrifugation. The final washed membrane pellet was suspended in a Tris (50 mM) buffer containing 120 mM NaCl, 5 mM KCl, 2 mM $CaCl_2$ and 10 mM $MgCl_2$ (pH 7.4) (buffer A). The [$^3$H]-DPCPX (([propyl-3H]8-cyclopentyl-1,3-dipropyxanthine); 0.6 nM) binding assay was carried out in 96-well plates in the presence of 2.5 $\mu$g of membrane protein, 0.5 mg of Ysi-poly-1-lysine SPA beads and 0.1 U adenosine deaminase in a final volume of 200 $\mu$l of buffer A. Non-specific binding was defined using xanthine amine congener (XAC; 2 $\mu$M). Compounds were tested at 10 concentrations from 10 $\mu$M–0.3 nM. All assays were conducted in duplicate and repeated at least two times. Assay plates were incubated for 1 hour at room temperature before centrifugation and then bound ligand determined using a Packard Topcount scintillation counter. $IC_{50}$ values were calculated using a non-linear curve fitting program and Ki values calculated using the Cheng-Prussoff equation.

Human Adenosine $A_{2a}$ Receptor

The gene encoding human adenosine $A_{2a}$ receptor was recombinantly introduced and expressed in chinese hamster ovary (CHO) cells using the semliki forest virus expression system. Cells were harvested, washed twice by centrifugation, homogenized and again washed by centrifugation. The final washed membrane pellet was suspended in a Tris (50 mM) buffer containing 120 mM NaCl, 5 mM KCl, 2 mM $CaCl_2$ and 10 mM $MgCl_2$ (pH 7.4) (buffer A). The [$^{125}$I]-AB-MECA ([N(6)-(4-amino-3-iodobenzyl)-5'-N-methylcarbamoyl-adenosine]; 0.05 nM) binding assay was carried out in 96-well a plates in the presence of 20 $\mu$g of membrane protein and 0.1 U adenosine deaminase in a final volume of 200 $\mu$g of buffer A. Non-specific binding was defined using xanthine amine congener (XAC; 2 $\mu$M). Compounds were tested at 10 concentrations from 10 $\mu$M–0.3 nM. All assays were conducted in duplicate and repeated at least two times. Assay plates were incubated for 1 hour at room temperature before filtration through Whatman Unifilter GF/C 96-well filter plates (preincubated with 0.3% polyethyleneimine). Filters were washed 3 times with 0.3 ml of cold (4° C.) Tris (50 mM)—NaC $R^1$is selected from the group consisting of unsubstituted phenyl, unsubstituted thiophenyl, and phenyl or thiophenyl substituted by one or two substituents selected from the group consisting of halogen, trifluoromethyl, lower alkyl, lower alkoxy, acetylamino, acetyl, lower alkenyl, —C(O)O-lower alkyl and thio-lower alkyl;

$R^2$ is selected from the group consisting of unsubstituted phenyl, unsubstituted thiophenyl and phenyl or thiophenyl substituted by one or two substituents selected from the group consisting of halogen, lower alkyl, halogen-lower alkyl and lower alkoxy. 1 (120 mM) buffer (pH 7.4). Microscint 40 scintillation fluid (50 $\mu$l) was added to each well and the wells sealed. After gentle shaking for 20 min, plates were counted on a Packard Topcount scintillation counter. $IC_{50}$ values were calculated using a non-linear curve fitting program and Ki values calculated using the Cheng-Prussoff equation.

In accordance with the invention, it has been shown that compounds of formula I have a high affinity toward the $A_{2A}$ receptor. In Table I below specific values of prepared compounds are described, Values of $KiHA_{2A}$ and $KiH_{A1}$ are shown in Table I for compounds of formula 1. A low Ki value is indicative of a particular compound's high affinity toward a particular receptor and conversely a higher Ki value is indicative of a lower affinity for that compound toward a particular receptor. A ratio obtained by dividing $KiH_{A1}$ by $KiHA_{2A}$ is then calculated and also displayed in Table I. This calculated ratio provides a measure of the selectivity of the compound between the $A_{2A}$ receptor and the $A_1$ receptor. Generally speaking, compounds that have a higher $HA_1/HA_{2A}$ ratio are able to give a substantially complete blockade of the $HA_{2A}$ receptor without substantially affecting the $A_1$ receptor.

The compounds of formula I and the pharmaceutically acceptable salts of the compounds of formula I can be used in a method of treatment e.g. in the form of pharmaceutical compositions. The pharmaceutical compositions can be administered orally, e.g. in the form of tablets, coated tablets, dragées, hard and soft gelatin capsules, solutions, emulsions or suspensions. The administration can, however, also be effected rectally, e.g. in the form of suppositories, parenterally, e.g. in the form of injection solutions.

The compounds of formula I can be processed with pharmaceutically inert, inorganic or organic carriers for the production of pharmaceutical compositions of the invention. Lactose, corn starch or derivatives thereof, talc, stearic acids or its salts and the like can be used, for example, as such carriers for tablets, coated tablets, dragees and hard gelatin capsules. Suitable carriers for soft gelatin capsules are, for example, vegetable oils, waxes, fats, semi-solid and liquid polyols and the like. Depending on the nature of the active substance no carriers are, however, usually required in the case of soft gelatin capsules. Suitable carriers for the production of solutions and syrups are, for example, water, polyols, glycerol, vegetable oil and the like. Suitable carriers for suppositories are, for example, natural or hardened oils, waxes, fats, semi-liquid or liquid polyols and the like.

The pharmaceutical compositions of the invention can, moreover, contain preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

Pharmaceutical compositions containing a therapeutically effective amount compound of formula I or a pharmaceutically acceptable salt thereof and a therapeutically inert carrier are also an object of the present invention, as is a process for their production, which comprises bringing one or more compounds of formula I and/or pharmaceutically acceptable acid addition salts and, if desired, one or more other therapeutically valuable substances into a galenical administration form together with one or more therapeutically inert carriers.

In accordance with the invention compounds of formula I as well as their pharmaceutically acceptable salts are useful in a method of treatment for control or prevention of illnesses based on the adenosine receptor antagonistic activity, such as Alzheimer's disease, Parkinson's disease, neuroprotection, schizophrenia, anxiety, pain, respiration deficits, depression, asthma, allergic responses, hypoxia, ischaemia, seizure and substance abuse. The method of treatment of the invention comprises administering a therapeutically effective amount of a compound of formula I or a pharmaceutically acceptable salt thereof to a patient in need of such treatment. Furthermore, a compound of formula I of the present invention may be useful as a sedative, muscle relaxant, antipsychotic, antiepileptic, anticonvulsant and cardioprotective agent and for the production of corresponding pharmaceutical compositions.

The most preferred indications in accordance with the present invention are those, which include disorders of the central nervous system, for example the treatment or prevention of certain depressive disorders, neuroprotection and Parkinson's disease.

The dosage can vary within wide limits and will, of course have to be adjusted to the individual requirements in each particular case. In the case of oral administration the dosage for adults can vary from about 0.01 mg to about 1000 mg per day of a compound of formula I or of the corresponding, amount of a pharmaceutically acceptable salt thereof. The daily dosage may be administered as single dose or in divided doses and, in addition, the Lipper limit can also be exceeded when this is found to be indicated.

Unless stated to the contrary, all of the examples listed below were prepared and characterized as indicated below.

EXAMPLE 1

N-(8-Methos-5-phenyl-[1,2,4]triazolo[1,5-a]pyridin-2-yl)-benzamide a 3-Methoxy-pyridin-2-yl-amine To a suspension of 33.2 g (0.592 mol) KOH in 80 ml DMSO was added 15.9 g (0.144 mol) 2-amino-3-hydroxypyridine and stirred for 90 min. Over a period of 60 min 9.9 ml (0.158 mol) methyl iodide was added and the Mixture stirred at room temperature for 14 h. The mixture was quenched with 450 ml water and extracted with 8×500 ml diethyl ether. The combined organic layer s were washed with water, dried with $MgSO_4$ and evaporated to dryness. The residue was recrystallized from ethyl acetate to yield 6.99 g (56.3 mmol, 39%) of the title compound as white crystals.

1-H-NMR (250 MHz-DMSO-d6): δ=7.49 (dd, $J_1$=5 Hz, $J_2$=1.4 Hz, 1H, H-4), 6.98 (dd, $J_1$=7.7 Hz, $J_2$=1.4 Hz, 1H, H-6), 6.48 (dd, $J_1$=7.7 Hz, $J_2$=5 Hz, 1H, H-5), 5.60 (s, br, 2H, $NH_2$), 3.75 (s, 3H, $OCH_3$).

b) N-(3-Methoxy -2-pyridinyl)-N'-carbyethoxy-thiourea

A mixture of 8 g (64 mmol) 3-methoxy-pyridin-2-ylamine and 7.29 ml (64 mmol) ethoxycarbonyl isothiocyanate (64 mmol) in 120 ml dioxane was stirred at room temperature for 1 h and evaporated to dryness to yield 16 g (62.7 mmol, 97%) of the title compound as yellow crystals.

1-H-NMR (250 MHz-DMSO-d6): δ=11.65 (s, br, 1H, NH), 11.09 (s, br, 1H, NH), 8.01 (dd, $J_1$=4.7 Hz, $J_2$=1.3 Hz, 1H, H-4), 7.53 (dd, $J_1$=7 Hz, $J_2$=1.3 Hz, 1H, H-6), 7.33 (dd, $J_1$=7 Hz, $J_2$=4.7 Hz, 1H, H-5), 4.22 (q, J=7.1 Hz, 2H, $CH_2$), 3.33 (s,3H, $OCH_3$), 1.26 (t, J=7.1 Hz, 3H, $CH_3$).

c) 8-Methoxy-[1,2,4]triazolo [1,5-a]pyridin-2-yl-amine

To a solution of 21.8 g (313.7 mmol) hydroxylamine hydrochloride and 32.2 ml (188.2 mmol) N-ethyldiisopropylamine in a mixture of 130 ml methanol ethanol 1:1 was added 16 g (62.7 mmol) N-(3-methoxy-2-pyridinyl)-N'-carboethoxy-thiourea and stirred for 2 h at room temperature and subsequently for 3 h at 60° C. The volatiles were removed under reduced pressure and the residue was triturated with 100 ml water. The collected precipitate was washed with 25 ml methanol/diethyl ether 4:1 and afterwards with 25 ml diethyl ether. After drying under high vacuum 8 g (78%, 48.7 mmol) of the title compound was collected as off-white crystals.

1-H-NMR (250 MHz-DMSO-d6): δ=8.13 (dd, $J_1$=6.6 Hz, $J_2$=1Hz, 1H, H-5), 6.89 (dd, $J_1$=7.1 Hz, $J_2$=1 Hz, 1H, H-7), 6.77 (dd, $J_1$=7.1 Hz, $J_2$=6.6 Hz, 1H, H-5), 5.88 (s, br, 2H, $NH_2$), 3.90 (s, 3H, $OCH_3$).

d) 5-Iodo-8-methoxy-[1,2,4]triazolo[1,5-a]pyridin-2-yl-amine

A mixture of 3 g (18.3 mmol) 8-methoxy-[1,2,4]triazolo[1,5-a]pyridin-2-yl-amine 6 ml water and 6 ml sulfuric acid (97%) was heated to 100° C. and 4.3 g (20.1 mmol) $KIO_3$ was added in portions over a period of 1 h. The mixture was heated to 120° C. for 3 h and another 6 ml water and 6 ml sulfuric acid (97%) was added. After cooling to 0° C. the precipitate was collected and washed with 2×15 ml water to yield the title compound as beige crystals. The mother liquid was treated with $Na_2CO_3$ and extracted with 5×250 ml DCM. The combined organic layers were dried with $MgSO_4$ and evaporated to dryness to yield an additional amount of the title compound. The product was recrystallized from ethanol to yield a total of 2.59 g (49%, 8.9 mmol) of the product.

1-H-NMR (250 MHz-DMSO-d6): δ=7.22 (d, J=8.2 Hz, 1H, H-7), 6.76 (d, J=8.2 Hz, 1H, H-6), 6.10 (s, br, 2H, $NH_2$), 3.89 (s, 3H, $OCH_3$). ps e) 8-Methoxy-5-phenyl-[1,2,4]triazolo[1,5-a]pyridin-2-yl-amine A mixture of 50 mg (0.17 mmol) 5-iodo-8-methoxy-[1,2,4]triazolo[1,5-a]pyridin-2-yl-amine, 46.2 mg (0.38 mmol) phenylboronic acid, 6.3 mg (0.008 mmol) dichloro[1,1'-bis(diphenylphosphino)ferrocene]palladium(II) dichloromethane adduct and 0.3 ml aqueous 2M $Na_2CO_3$ solution in 1 ml dioxane was heated for 90 min to 80° C. The mixture was filtered over a short silica pad and eluted with 30 ml ethyl acetate. The filtrate is concentrated under reduced pressure and the residue was purified by preparative HPLC on reversed phase eluting with a water/acetonitrile gradient to yield 12 mg (29%) of the title compound.

MS m/e (%): 241.3 ($MH^+$, 100); 1-H-NMR (250 MHz-DMSO-d6): δ=7.82 (dd, $J_1$=8.1 Hz, $J_2$=1 Hz, 2H, phenyl), 7.48 (m, 3H, phenyl), 6.81 (dd, $J_1$=8.4 Hz, $J_2$=1 Hz, 2H, H-6 and H-7), 4.53 (s, br, 2H, $NH_2$), 4.03 (s, 3H, $OCH_3$).

f) N-(8-Methoxy-5-phenyl-[1,2,4]triazolol[5-a]pyridin-2-yl)-benzamide

A mixture of 30 mg (0.125 mmol) 8-methoxy-5-phenyl-[1,2,4]triazolo[1,5-a]pyridin-2-yl-amine, 19.2 mg (0.137 mmol) benzoyl chloride and 27 mg $NEt_3$ in 0.5 ml dioxane was shaken at room temperature for 4 d. After addition of 0.05 ml formic acid the mixture was directly subjected to preparative HPLC on reversed phase eluting with a water/acetonitrile gradient to yield 8.6 mg (19%) of the title compound.

MS m/e (%): 345 ($MH^+$, 100); 1-H-NMR (500 MHz, DMSO) δ=7.95 (m, 4H, Ph), 7.61(m, 6H, Ph), 7.30 (m, 3H, Ph/NH), 4.05 (s, 3H, s, $OCH_3$).

According to example 1 further [1,2,4]triazolol[1,5-a]ppyridin-derivatives have been synthesized. The results are compiled in Table I comprising example 2 to example 51.

TABLE I

| No | hA2a Ki(nM) | hA1 Ki(nM) | Selectivity A1/A2a | Structure | Name | MW | MS m/e (%) |
|---|---|---|---|---|---|---|---|
| 2 | 63.6 | 2389.7 | 37.6 | 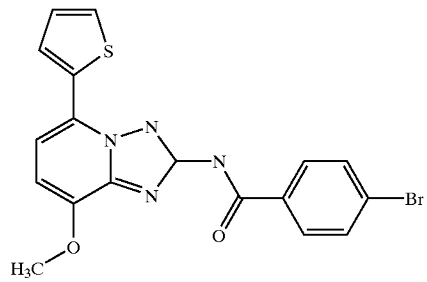 | 4-Bromo-N-(8-methoxy-5-thiophen-2-yl-[1,2,4]triazolo[1,5-a]pyridin-2-yl)-benzamide | 429.3 | MH$^+$ (100) |
| 3 | 175.5 | 2032.8 | 11.6 | 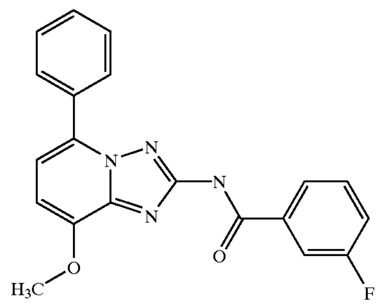 | 3-Fluoro-N-(8-methoxy-5-phenyl-[1,2,4]triazolo[1,5-a]pyridin-2-yl)-benzamide | 362.4 | MH$^+$ (100) |
| 4 | 114.4 | 2240.7 | 19.6 | 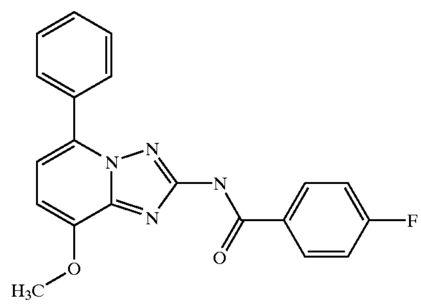 | 4-Fluoro-N-(8-methoxy-5-phenyl-[1,2,4]triazolo[1,5-a]pyridin-2-yl)-benzamide | 362.4 | MH$^+$ (100) |
| 5 | 257.7 | 1868.3 | 7.3 | 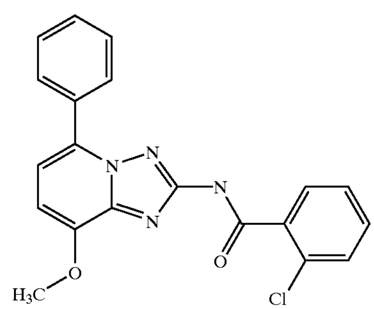 | 2-Chloro-N-(8-methoxy-5-phenyl-[1,2,4]triazolo[1,5-a]pyridin-2-yl)-benzamide | 378.8 | MH$^+$ (100) |
| 6 | 181.3 | 2867.6 | 15.8 | 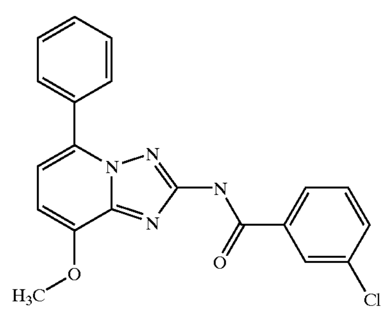 | 3-Chloro-N-(8-methoxy-5-phenyl-[1,2,4]triazolo[1,5-a]pyridin-2-yl)-benzamide | 378.8 | MH$^+$ (100) |

TABLE I-continued

| No | hA2a Ki(nM) | hA1 Ki(nM) | Selectivity A1/A2a | Structure | Name | MW | MS m/e (%) |
|----|---|---|---|---|---|---|---|
| 7 | 226.8 | 4714.1 | 20.8 | 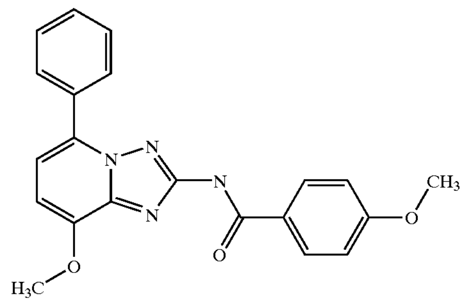 | 4-Methoxy-N-(8-methoxy-5-phenyl-[1,2,4]triazolo[1,5-a]pyridin-2-yl)-benzamide | 374.4 | MH+ (100) |
| 8 | 136.5 | 2880.0 | 21.1 | 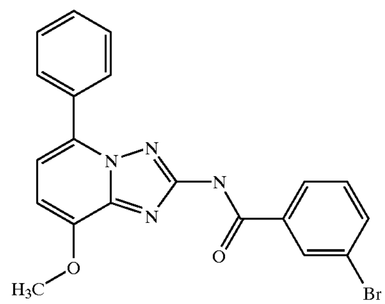 | 3-Bromo-N-(8-methoxy-5-phenyl-[1,2,4]triazolo[1,5-a]pyridin-2-yl)-benzamide | 423.3 | MH+ (100) |
| 9 | 102.3 | 2293.4 | 22.4 | 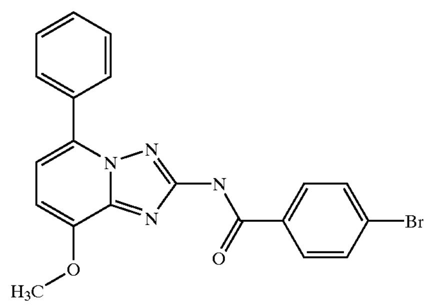 | 4-Bromo-N-(8-methoxy-5-phenyl-[1,2,4]triazolo[1,5-a]pyridin-2-yl)-benzamide | 423.3 | MH+ (100) |
| 10 | 173.5 | 2001.7 | 11.5 | 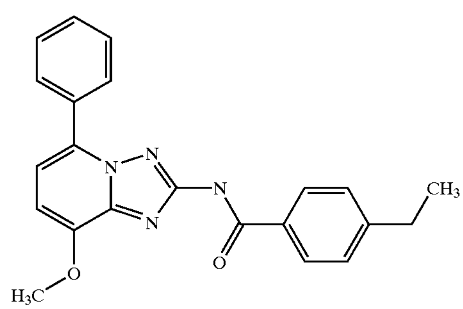 | 4-Ethyl-N-(8-methoxy-5-phenyl-[1,2,4]triazolo[1,5-a]pyridin-2-yl)-benzamide | 372.4 | MH+ (100) |
| 11 | 158.6 | 3705.5 | 23.4 | 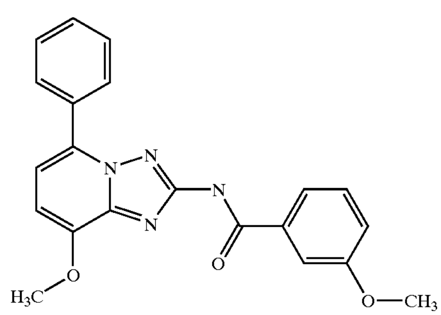 | 3-Methoxy-N-(8-methoxy-5-phenyl-[1,2,4]triazolo[1,5-a]pyridin-2-yl)-benzamide | 374.4 | MH+ (100) |

TABLE I-continued

| No | hA2a Ki(nM) | hA1 Ki(nM) | Selectivity A1/A2a | Structure | Name | MW | MS m/e (%) |
|---|---|---|---|---|---|---|---|
| 12 | 111.6 | 2150.7 | 19.3 | 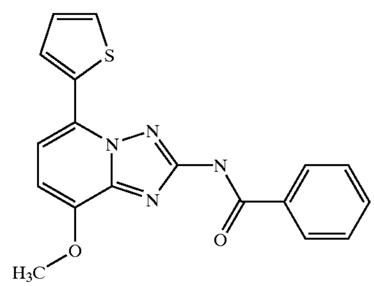 | N-(8-Methoxy-5-thiophen-2-yl-[1,2,4]triazolo[1,5-a]pyridin-2-yl)-benzamide | 350.4 | MH+ (100) |
| 13 | 229.8 | 2246.9 | 9.8 | 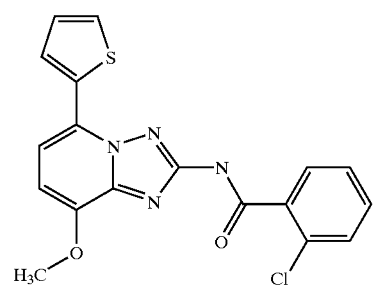 | 2-Chloro-N-(8-methoxy-5-thiophen-2-yl-[1,2,4]triazolo[1,5-a]pyridin-2-yl)-benzamide | 384.8 | MH+ (100) |
| 14 | 142.5 | 2482.8 | 17.4 | 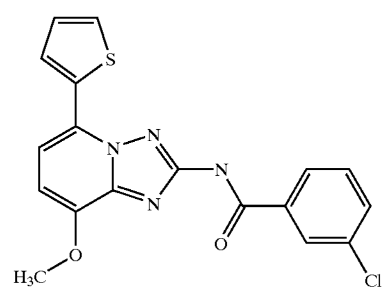 | 3-Chloro-N-(8-methoxy-5-thiophen-2-yl-[1,2,4]triazolo[1,5-a]pyridin-2-yl)-benzamide | 384.8 | MH+ (100) |
| 15 | 113.9 | 2911.0 | 25.6 | 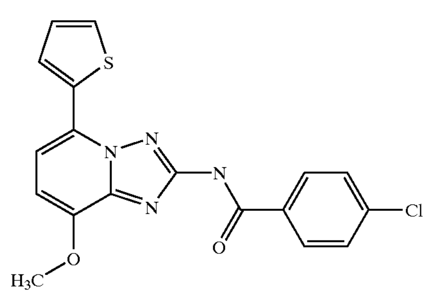 | 4-Chloro-N-(8-methoxy-5-thiophen-2-yl-[1,2,4]triazolo[1,5-a]pyridin-2-yl)-benzamide | 384.8 | MH+ (100) |
| 16 | 238.1 | 3376.6 | 14.2 | 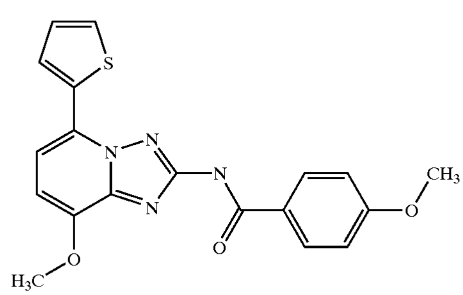 | 4-Methoxy-N-(8-methoxy-5-thiophen-2-yl-[1,2,4]triazolo[1,5-a]pyridin-2-yl)-benzamide | 380.4 | MH+ (100) |

TABLE I-continued

| No | hA2a Ki(nM) | hA1 Ki(nM) | Selectivity A1/A2a | Structure | Name | MW | MS m/e (%) |
|---|---|---|---|---|---|---|---|
| 17 | 207.9 | 2489.0 | 12.0 | 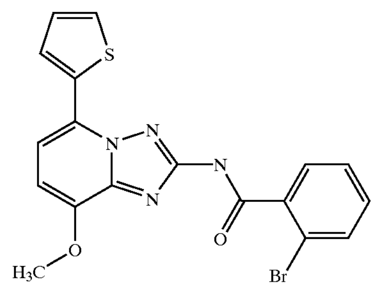 | 2-Bromo-N-(8-methoxy-5-thiophen-2-yl-[1,2,4]triazolo[1,5-a]pyridin-2-yl)-benzamide | 429.3 | MH+ (100) |
| 18 | 136.3 | 3302.1 | 24.2 | 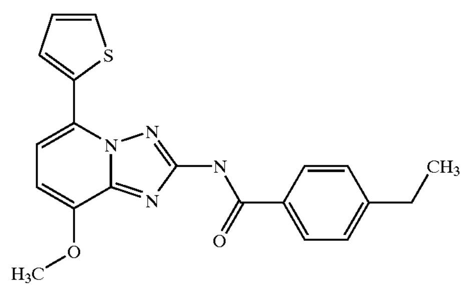 | 4-Ethyl-N-(8-methoxy-5-thiophen-2-yl-[1,2,4]triazolo[1,5-a]pyridin-2-yl)-benzamide | 378.5 | MH+ (100) |
| 19 | 200.9 | 4937.6 | 24.6 | 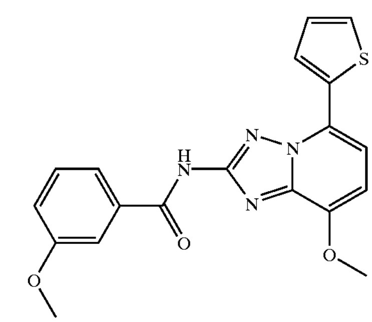 | 3-Methoxy-N-(8-methoxy-5-thiophen-2-yl-[1,2,4]triazolo[1,5-a]pyridin-2-yl)-benzamide | 380.4 | MH+ (100) |
| 20 | 207.7 | 3295.9 | 15.9 | 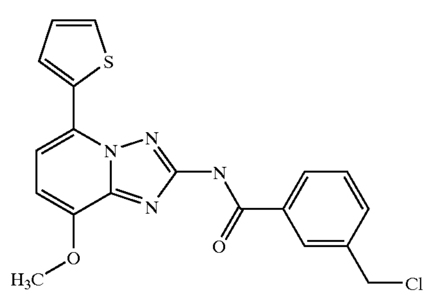 | 3-Chloromethyl-N-(8-methoxy-5-thiophen-2-yl-[1,2,4]triazolo[1,5-a]pyridin-2-yl)-benzamide | 398.9 | MH+ (100) |
| 21 | 384.1 | | | 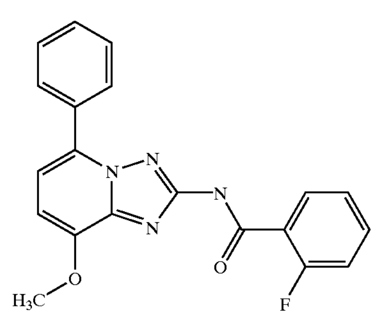 | 2-Fluoro-N-(8-methoxy-5-phenyl-[1,2,4]triazolo[1,5-a]pyridin-2-yl)-benzamide | 362.4 | MH+ (100) |

TABLE I-continued

| No | hA2a Ki(nM) | hA1 Ki(nM) | Selectivity A1/A2a | Structure | Name | MW | MS m/e (%) |
|----|----|----|----|----|----|----|----|
| 22 | 266.2 | | | 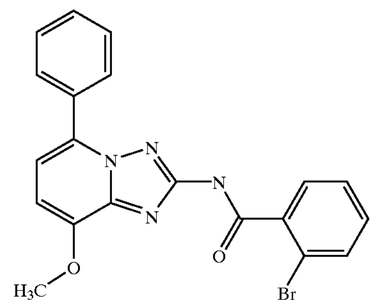 | 2-Bromo-N-(8-methoxy-5-phenyl-[1,2,4]triazolo[1,5-a]pyridin-2-yl)-benzamide | 423.3 | MH$^+$ (100) |
| 23 | 65.1 | 2827.2 | 43.4 | 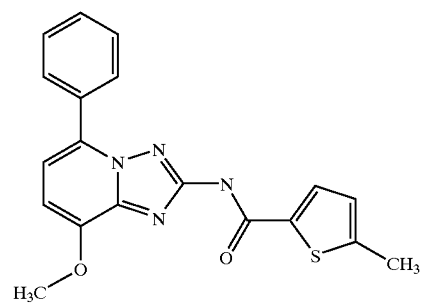 | 5-Methyl-thiophene-2-carboxylic acid(8-methoxy-5-phenyl-[1,2,4]triazolo[1,5-a]pyridin-2-yl)-amide | 364.4 | MH$^+$ (100) |
| 24 | 133.7 | 2613.1 | 19.5 | 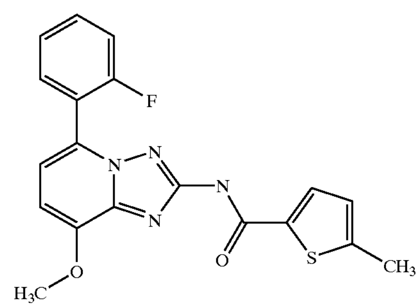 | 5-Methyl-thiophene-2-carboxylic acid [5-(2-fluoro-phenyl)-8-methoxy-[1,2,4]triazolo[1,5-a]pyridin-2-yl]-amide | 382.4 | MH$^+$ (100) |
| 25 | 164.9 | 2091.7 | 12.7 | 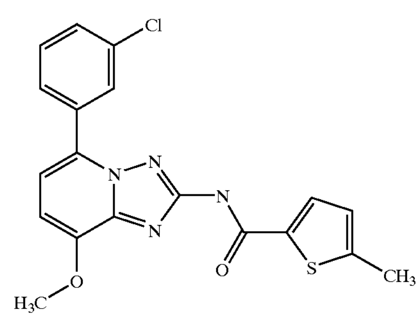 | 5-Methyl-thiophene-2-carboxylic acid [5-(3-chloro-phenyl)-8-methoxy-[1,2,4]triazolo[1,5-a]pyridin-2-yl]-amide | 398.9 | MH$^+$ (100) |

TABLE I-continued

| No | hA2a Ki(nM) | hA1 Ki(nM) | Selectivity A1/A2a | Structure | Name | MW | MS m/e (%) |
|---|---|---|---|---|---|---|---|
| 26 | 256.4 | 2855.2 | 11.1 | 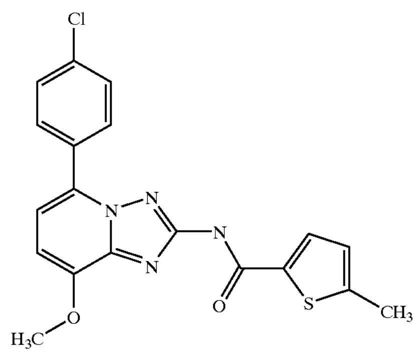 | 5-Methyl-thiophene-2-carboxylic acid [5-(4-chloro-phenyl)-8-methoxy-[1,2,4]triazolo[1,5-a]pyridin-2-yl]-amide | 398.9 | MH+ (100) |
| 27 | 106.6 | 1762.8 | 16.5 | 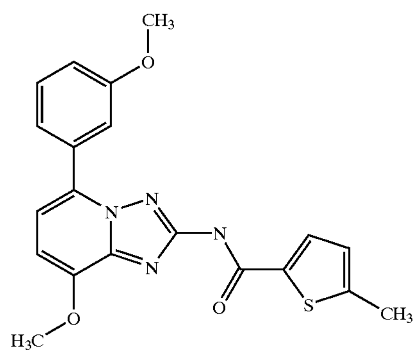 | 5-Methyl-thiophene-2-carboxylic acid [8-methoxy-5-(3-methoxy-phenyl)-[1,2,4]triazolo[1,5-a]pyridin-2-yl]-amide | 394.5 | MH+ (100) |
| 28 | 142.8 | 5210.7 | 36.5 | 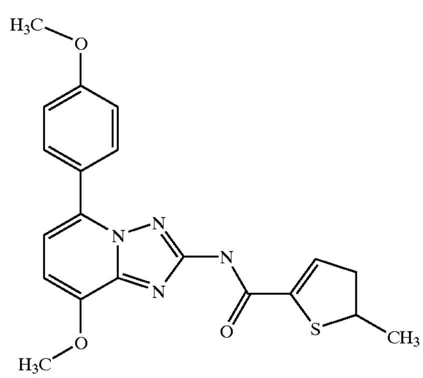 | 5-Methyl-thiophene-2-carboxylic acid [8-methoxy-5-(4-methoxy-phenyl)[1,2,4]triazolo[1,5-a]pyridin-2-yl]-amide | 394.5 | MH+ (100) |
| 29 | 71.1 | 1719.3 | 24.2 | 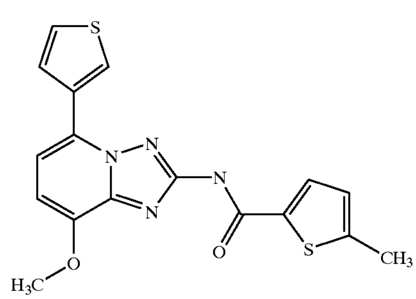 | 5-Methyl-thiophene-2-carboxylic acid (8-methoxy-5-thiophen-3-yl-[1,2,4]triazolo[1,5-a]pyridin-2-yl)-amide | 370.5 | MN+ (100) |

TABLE I-continued

| No | hA2a Ki(nM) | hA1 Ki(nM) | Selectivity A1/A2a | Structure | Name | MW | MS m/e (%) |
|---|---|---|---|---|---|---|---|
| 30 | 72.9 | 1356.2 | 18.6 | 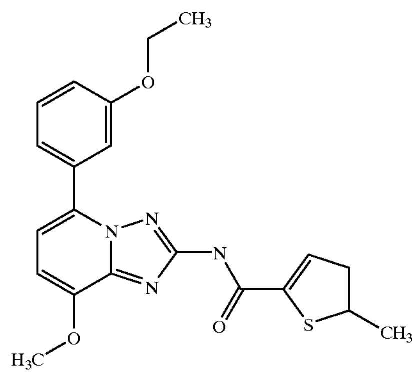 | 5-Methyl-thiophene-2-carboxylic acid [5-(3-ethoxy-phenyl)-8-methoxy-[1,2,4]triazolo[1,5-a]pyridin-2-yl]-amide | 408.5 | MH+ (100) |
| 31 | 29.5 | 1166.9 | 39.6 | 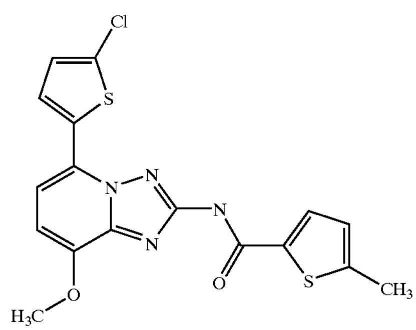 | 5-Methyl-thiophene-2-carboxylic acid [5-(5-chloro-thiophen-2-yl)-8-methoxy-[1,2,4]triazolo[1,5-a]pyridin-2-yl]-amide | 404.9 | MH+ (100) |
| 32 | 229.0 | 5642.1 | 24.6 | 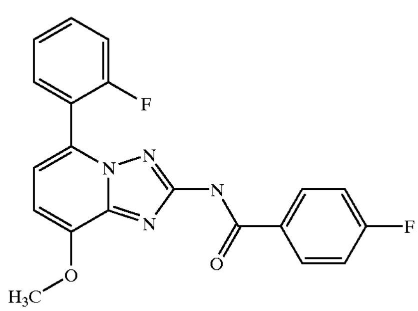 | 4-Fluoro-N-[5-(2-fluoro phenyl)-8-methoxy-[1,2,4]triazolo[1,5-a]pyridin-2-yl]-benzamide | 380.4 | MH+ (100) |
| 33 | 191.1 | 2343.1 | 12.3 | 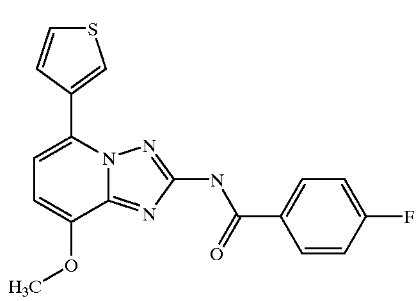 | 4-Fluoro-N-(8-methoxy-5-thiophen-3-yl-[1,2,4]triazolo[1,5-a]pyridin-2-yl)-benzamide | 368.4 | MH+ (100) |

TABLE I-continued

| No | hA2a Ki(nM) | hA1 Ki(nM) | Selectivity A1/A2a | Structure | Name | MW | MS m/e (%) |
|---|---|---|---|---|---|---|---|
| 34 | 132.7 | 1492.8 | 11.2 | 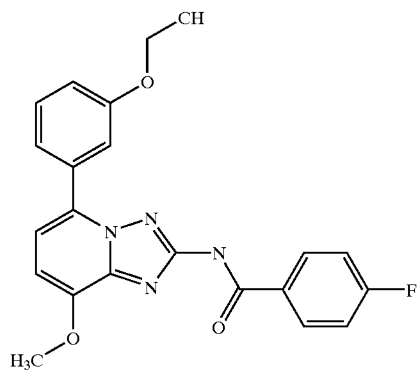 | N-[5-(3-Ethoxy-phenyl)-8-methoxy-[1,2,4]triazolo[1,5-a]pyridin-2-yl]-4-fluoro-benzamide | 406.4 | MH+ (100) |
| 35 | 127.5 | 1356.2 | 10.6 | 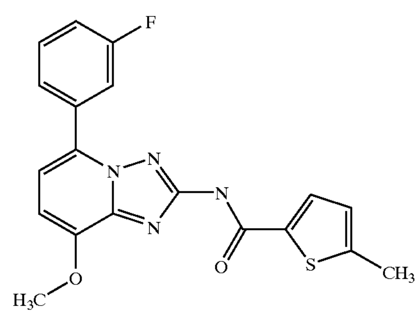 | 5-Methyl-thiophene-2-carboxylic acid [5-(3-fluoro-phenyl)-8-methoxy-[1,2,4]triazolo[1,5-a]pyridin-2-yl]-amide | 382.4 | MH+ (100) |
| 36 | 526.9 | | | 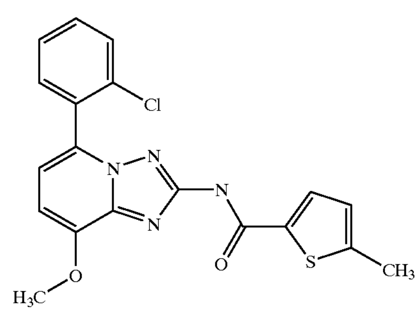 | 5-Methyl-thiophene-2-carboxylic acid [5-(2-chloro-phenyl)-8-methoxy-[1,2,4]triazolo[1,5-a]pyridin-2-yl]-amide | 398.9 | MH+ (100) |
| 37 | 937.7 | | | 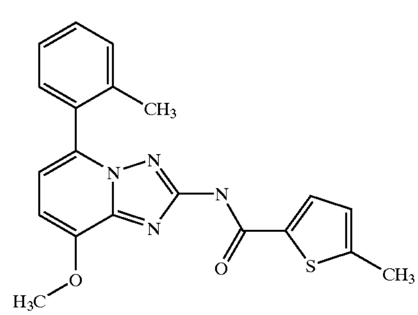 | 5-Methyl-thiophene-2-carboxylic acid (8-methoxy-5-o-tolyl-[1,2,4]triazolo[1,5-a]pyridin-2-yl)-amide | 378.5 | MH+ (100) |

TABLE I-continued

| No | hA2a Ki(nM) | hA1 Ki(nM) | Selectivity A1/A2a | Structure | Name | MW | MS m/e (%) |
|---|---|---|---|---|---|---|---|
| 38 | 276.8 | | | 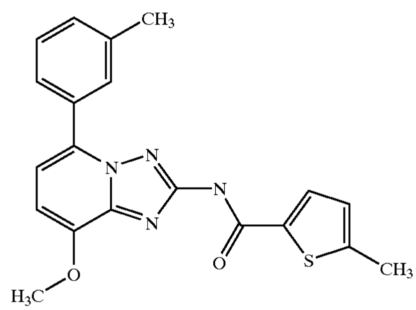 | 5-Methyl-thiophene-2-carboxylic acid (8-methoxy-5-m-tolyl [1,2,4]triazolo[1,5-a]pyridin-2-yl)-amide | 378.5 | MH+ (100) |
| 39 | 451.0 | | | 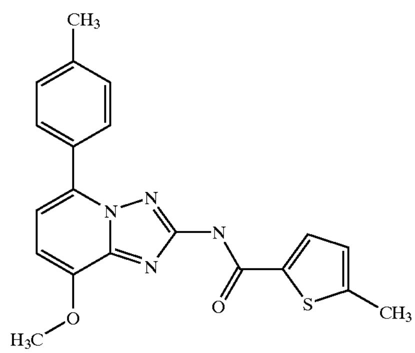 | 5-Methyl-thiophene-2-carboxylic acid (8-methoxy-5-p-tolyl-[1,2,4]triazolo[1,5-a]pyridin-2-yl)-amide | 378.5 | MH+ (100) |
| 40 | 547.0 | | | 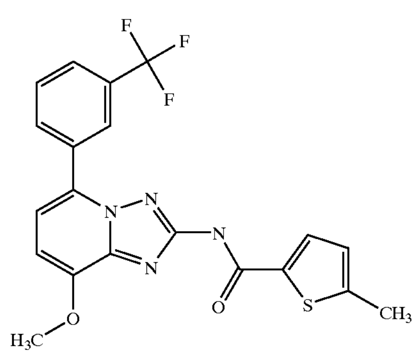 | 5-Methyl-thiophene-2-carboxylic acid [8-methoxy-5-(3-trifluoromethyl-phenyl)-[1,2,4]triazolo[1,5-a]pyridin-2-yl]-amide | 432.4 | MH+ (100) |
| 41 | 254.4 | | | 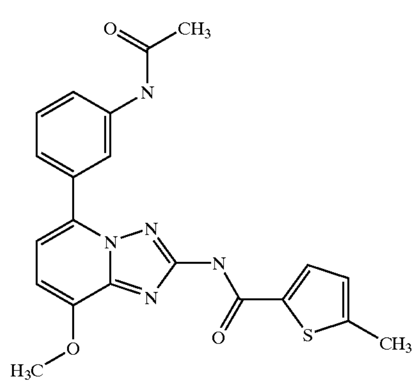 | 5-Methyl-thiophene-2-carboxylic acid [5-(3-acetylamino-phenyl)-8-methoxy-[1,2,4]triazolo[1,5-a]pyridin-2-yl]-amide | 421.5 | MH+ (100) |

TABLE I-continued

| No | hA2a Ki(nM) | hA1 Ki(nM) | Selectivity A1/A2a | Structure | Name | MW | MS m/e (%) |
|---|---|---|---|---|---|---|---|
| 42 | 287.1 | | | 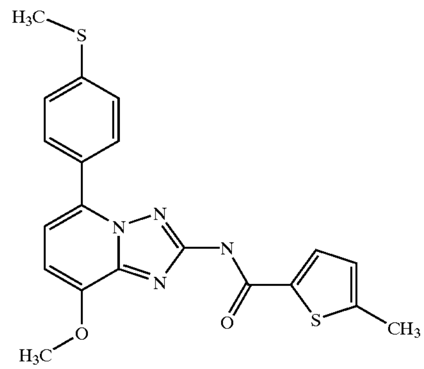 | 5-Methyl-thiophene-2-carboxylic acid [8-methoxy-5-(4-methylsulfanyl-phenyl)-[1,2,4]triazolo[1,5-a]pyridin-2-yl]-amide | 410.5 | MH+ (100) |
| 43 | 618.4 | | | 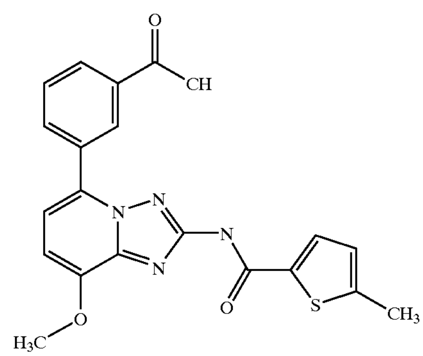 | 5-Methyl-thiophene-2-carboxylic acid [5-(3-acetyl-phenyl)-8-methoxy-[1,2,4]triazolo[1,5-a]pyridin-2-yl]-amide | 406.5 | MH+ (100) |
| 44 | 246.1 | | | 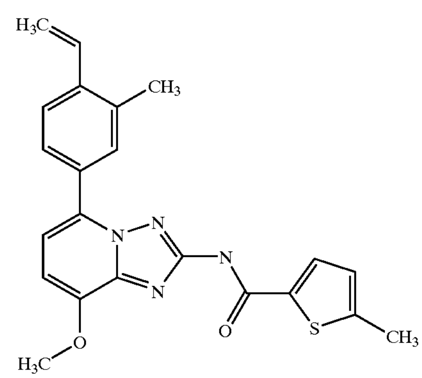 | 5-Methyl-thiophene-2-carboxylic acid [8-methoxy-5-(4-vinyl-phenyl)-[1,2,4]triazolo[1,5-a]pyridin-2-yl]-amide | 390.5 | MH+ (100) |
| 45 | 852.2 | | | 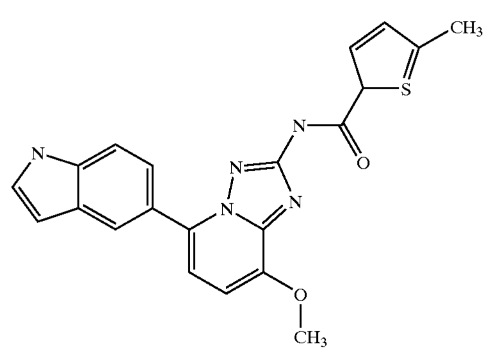 | 5-Methyl-thiophene-2-carboxylic acid [5-(1H-indol-5-yl)-8-methoxy-[1,2,4]triazolo[1,5-a]pyridin-2-yl]-amide | 403.5 | MH+ (100) |

TABLE I-continued

| No | hA2a Ki(nM) | hA1 Ki(nM) | Selectivity A1/A2a | Structure | Name | MW | MS m/e (%) |
|----|-------------|------------|--------------------|-----------|------|-----|------------|
| 46 | 331.8 | | | 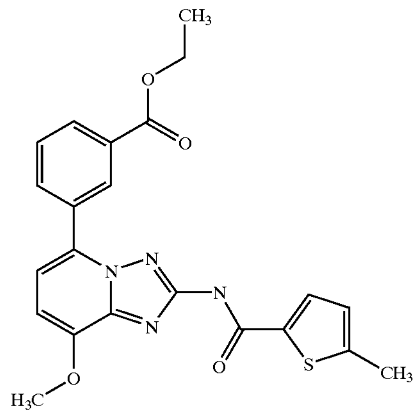 | 3-{8-Methoxy-2-[(5-methyl-thiophene-2-carbonyl)-amino]-[1,2,4]triazolo[1,5-a]pyridin-5-yl}-benzoic acid ethyl ester | 436.5 | MH+ (100) |
| 47 | 269.2 | | | 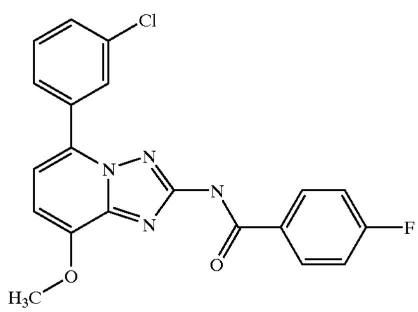 | N-[5-(3-Chloro-phenyl)-8-methoxy-[1,2,4]triazolo[1,5-a]pyridin-2-yl]-4-fluoro-benzamide | 396.8 | MH+ (100) |
| 48 | 623.5 | | | 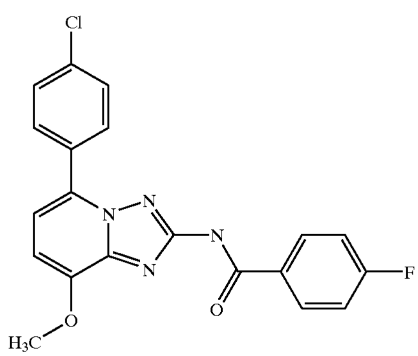 | N-[5-(4-Chloro-phenyl)-8-methoxy-[1,2,4]triazolo[1,5-a]pyridin-2-yl]-4-fluoro-benzamide | 396.8 | MH+ (100) |
| 49 | 346.4 | | | 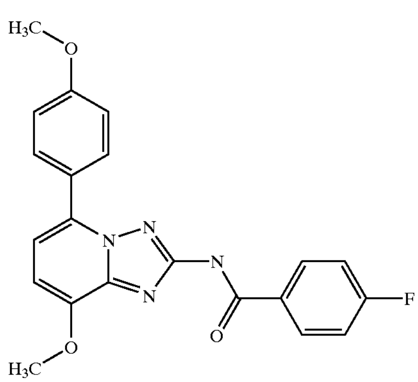 | 4-Fluoro-N-[8-methoxy-5-(4-methoxy-phenyl)-[1,2,4]triazolo[1,5-a]pyridin-2-yl]-benzamide | 392.4 | MH+ (100) |

TABLE I-continued

| No | hA2a Ki(nM) | hA1 Ki(nM) | Selectivity A1/A2a | Structure | Name | MW | MS m/e (%) |
|---|---|---|---|---|---|---|---|
| 50 | 854.7 | | | 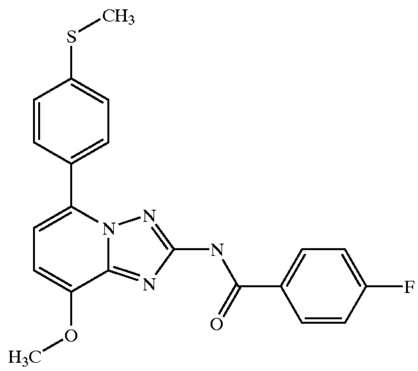 | 4-Fluoro-N-[8-methoxy-5-(4-methylsulfanyl-phenyl)-[1,2,4]triazolo[1,5-a]pyridin-2-yl]-benzamide | 408.5 | MH+ (100) |
| 51 | 479.9 | | | 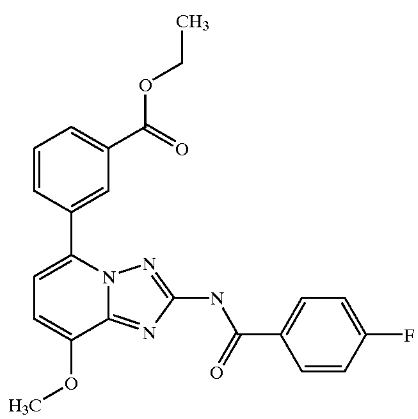 | 3-[2-(4-Fluoro-benzoylamino)-8-methoxy-[1,2,4]triazolo[1,5-a]pyridin-5-yl]-benzoic acid ethyl ester | 434.4 | MH+ (100) |

| Tablet Formulation (Wet Granulation) | | | | | | Capsule Formulation | | | | | |
|---|---|---|---|---|---|---|---|---|---|---|---|
| | | mg/tablet | | | | | | mg/capsule | | | |
| Item | Ingredients | 5 mg | 25 mg | 100 mg | 500 mg | Item | Ingredients | 5 mg | 25 mg | 100 mg | 500 mg |
| 1. | Compound of formula 1 | 5 | 25 | 100 | 500 | 1. | Compound of formula 1 | 5 | 25 | 100 | 500 |
| 2. | Lactose Anhydrous DTG | 125 | 105 | 30 | 150 | 2. | Hydrous Lactose | 159 | 123 | 148 | — |
| 3. | Sta-Rx 1500 | 6 | 6 | 6 | 30 | 3. | Corn Starch | 25 | 35 | 40 | 70 |
| 4. | Microcrystalline Cellulose | 30 | 30 | 30 | 150 | 4. | Talc | 10 | 15 | 10 | 25 |
| 5. | Magnesium Stearate | 1 | 1 | 1 | 1 | 5. | Magnesium Stearate | 1 | 2 | 2 | 5 |
| | Total | 167 | 167 | 167 | 831 | | Total | 200 | 200 | 300 | 600 |

Manufacturing Procedure

1. Mix items 1, 2, 3 and 4 and granulate with purified water.
2. Dry the granules at 50° C.
3. Pass the granules through suitable milling equipment.
4. Add item 5 and mix for three minutes; compress on a suitable press.

Manufacturing Procedure

1. Mix items 1, 2 and 3 in a suitable mixer for 30 minutes.
2. Add items 4 and 5 and mix for 3 minutes.
3. Fill into a suitable capsule.

What is claimed is:

1. A compound of formula

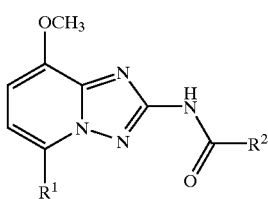

or a pharmaceutically acceptable salt thereof, wherein
$R^1$ is selected from the group consisting of unsubstituted phenyl, unsubstituted thiophenyl, and phenyl or thiophenyl substituted by one or two substituents selected from the group consisting of halogen, trifluoromethyl, lower alkyl, lower alkoxy, acetylamino, acetyl, lower alkenyl, —C(O)O-lower alkyl and thio-lower alkyl; and
$R^2$ is selected from the group consisting of unsubstituted phenyl, unsubstituted thiophenyl and phenyl or thiophenyl substituted by one or two substituents selected from the group consisting of halogen, lower alkyl, halogen-lower alkyl and lower alkoxy.

2. A compound of formula I in accordance with claim 1, wherein $R^1$ is unsubstituted thiophenyl and $R^2$ is selected from the group consisting of unsubstituted phenyl and phenyl substituted by halogen or lower alkyl.

3. A compound of formula I in accordance with claim 2, wherein the compound is selected from the group consisting of
   4-bromo-N-(8-methoxy-5-thiophen-2-yl-[1,2,4]triazolo[1,5-a]pyridin-2-yl)-benzamide,
   N-(8-methoxy-5-thiophen-2-yl-[1,2,4]triazolo[1,5-a]pyridin-2-yl)-benzamide,
   3-chloro-N-(8-methoxy-5-thiophen-2-yl-[1,2,4]triazolo[1,5-a]pyridin-2-yl)-benzamide,
   4-chloro-N-(8-methoxy-5-thiophen-2-yl-[1,2,4]triazolo[1,5-a]pyridin-2-yl)-benzamide and
   4-ethyl-N-(8-methoxy-5-thiophen-2-yl-[1,2,4]triazolo[1,5-a]pyridin-2-yl)-benzamide.

4. A compound of formula I in accordance with claim 1, wherein $R^1$ is selected from the group consisting of unsubstituted phenyl and phenyl substituted by lower alkoxy and wherein $R^2$ is selected from the group consisting of unsubstituted phenyl and phenyl substituted by halogen.

5. A compound of formula I in accordance with claim 4, wherein the compound is selected from the group consisting of
   4-fluoro-N-(8-methoxy-5-phenyl-[1,2,4]triazolo[1,5-a]pyridin-2-yl)-benzamide,
   3-bromo-N-(8-methoxy-5-phenyl-[1,2,4]triazolo[1,5-a]pyridin-2-yl)-benzamide,
   4-bromo-N-(8-methoxy-5-phenyl-[1,2,4]triazolo[1,5-a]pyridin-2-yl)-benzamide and
   N-[5-(3-ethoxy-phenyl)-8-methoxy-[1,2,4]triazolo[1,5-a]pyridin-2-yl]-4-fluoro-benzamide.

6. A compound of formula I in accordance with claim 1, wherein $R^1$ is selected from the (group consisting of unsubstituted phenyl, and phenyl substituted by a substitutent selected from the group halogen and lower alkoxy; and $R^2$ is selected from the group consisting of unsubstituted thiophenyl and thiophenyl substituted by lower alkyl.

7. A compound of formula I in accordance with claim 6, wherein the compound is selected from the group consisting of
   5-methyl-thiophene-2-carboxylic acid (8-methoxy-5-phenyl-[1,2,4]triazolo[1,5-a]pyridin-2-yl)-amide,
   5-methyl-thiophene-2-carboxylic acid [5-(2-fluoro-phenyl)-8-methoxy-[1,2,4]triazolo[1,5-a]pyridin-2-yl]-amide,
   5-methyl-thiophene-2-carboxylic acid [8-methoxy-5-(3-methoxy-phenyl)-[1,2,4]triazolo[1,5-a]pyridin-2-yl]-amide,
   5-methyl-thiophene-2-carboxylic acid [8-methoxy-5-(4-methoxy-phenyl)-[1,2,4]triazolo[1,5-a]pyridin-2-yl]-amide,
   5-methyl-thiophene-2-carboxylic acid [5-(3-ethoxy-phenyl)-8-methoxy-[1,2,4]triazolo[1,5-a]pyridin-2-yl]-amide and
   5-methyl-thiophene-2-carboxylic acid [5-(3-fluoro-phenyl)-8-methoxy-[1,2,4]triazolo[1,5-a]pyridin-2-yl]-amide.

8. A compound of formula I in accordance with claim 1, wherein $R^1$ is selected from the group consisting of unsubstituted thiophenyl and thiophenyl substituted by halogen; and $R^2$ is selected from the group consisting of unsubstituted thiophenyl and thiophenyl substituted by lower alkyl.

9. A compound of formula I in accordance with claim 8, wherein the compound is selected from the group consisting of
   5-methyl-thiophene-2-carboxylic acid (8-methoxy-5-thiophen-3-yl-[1,2,4]triazolo[1,5-a]pyridin-2-yl)-amide and
   5-methyl-thiophene-2-carboxylic acid [5-(5-chloro-thiophen-2-yl)-8-methoxy-[1,2,4]triazolo[1,5-a]pyridin-2-yl]-amide.

10. A pharmaceutical composition containing a therapeutically effective amount of at least one compound of formula I according to claim 1, or a pharmaceutically acceptable salt thereof, and at least one pharmaceutically acceptable excipient.

11. A method of treatment of a disease mediated by the adenosine $A_{2A}$ receptor comprising administering a therapeutically effective amount of a compound of formula I according to claim 1 to a patient in need of such treatment.

12. A process for preparing a compound of formula I as defined in claim 1, comprising
a) reacting a compound of formula

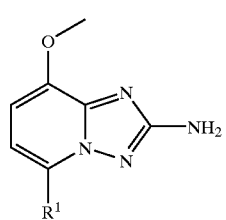

with a compound of formula $R^2$COCl                         III forming a compound of formula

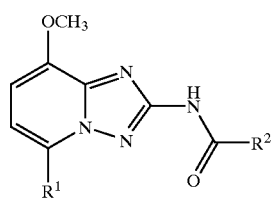

wherein
$R^1$ is selected from the group consisting of unsubstituted phenyl, unsubstituted thiophenyl, and phenyl or thiophenyl substituted by one or two substituents selected from the group consisting of halogen, trifluoromethyl, lower alkyl, lower alkoxy, acetylamino, acetyl, lower alkenyl, —C(O)O-lower alkyl and thio-lower alkyl; and R² is selected from the group consisting of unsubstituted phenyl, unsubstituted thiophenyl and phenyl or thiophenyl substituted by one or two substituents selected from the group consisting of halogen, lower alkyl, halogen-lower alkyl and lower alkoxy.

13. A process for preparing a compound of formula I in accordance with claim 1, comprising reacting a compound of formula

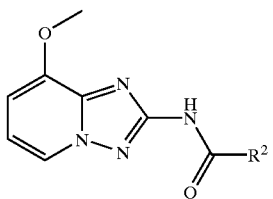

IV with KIO₃
forming a compound of formula

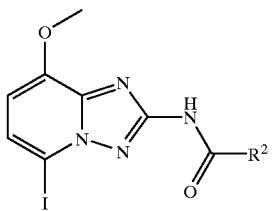

V and then reacting compound V with a compound of formula

R¹—B(OH)₂ VIa or

R¹—B(OH)₂ or

VIa

-continued

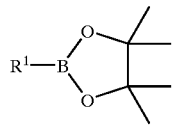

VIb forming a compound of formula

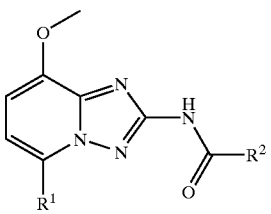

I wherein

R¹ is selected from the group consisting of unsubstituted phenyl, unsubstituted thiophenyl, and phenyl or thiophenyl substituted by one or two substituents selected from the group consisting of halogen, trifluoromethyl, lower alkyl, lover alkoxy, acetylamino, acetyl, lower alkenyl, —C(O)O-lower alkyl and thio-lower alkyl; and R² is selected from the group consisting of unsubstituted phenyl, unsubstituted thiophenyl and phenyl or thiophenyl substituted by one or two substituents selected from the group consisting of halogen, lower alkyl, halogen-lower alkyl and lower alkoxy.

14. A method of treatment or prevention of depressive disorders, Parkinson's disease or Alzheimer's disease comprising administering a therapeutically effective amount of a compound of formula I according to claim 1 to a patient in need of such treatment.

* * * * *

UNITED STATES PATENT AND TRADEMARK OFFICE
CERTIFICATE OF CORRECTION

PATENT NO.    : 6,514,989 B1
DATED         : February 4, 2003
INVENTOR(S)   : Nettekoven et al.

It is certified that error appears in the above-identified patent and that said Letters Patent is hereby corrected as shown below:

<u>Column 41,</u>
Line 42, delete "$R^1$-B(OH)$_2$ or VIa," second instance.

Signed and Sealed this

Twenty-second Day of July, 2003

JAMES E. ROGAN
*Director of the United States Patent and Trademark Office*